United States Patent [19]

Sbarbaro

[11] Patent Number: 5,011,974

[45] Date of Patent: Apr. 30, 1991

[54] PROCESS FOR THE PREPARATION OF DERIVATIVE OF 2-DIETHYLAMINO-1-METHYLETHYL-1-HYDROXY-(BICYCLOHEXYL)-2-CARBOXYLATE

[75] Inventor: Franco Sbarbaro, S. Olcese, Italy

[73] Assignee: Laboratori Guidotti, Pisa, Italy

[21] Appl. No.: 318,520

[22] Filed: Mar. 1, 1989

Related U.S. Application Data

[63] Continuation of Ser. No. 27,085, Mar. 16, 1987, abandoned, which is a continuation of Ser. No. 479,646, Mar. 28, 1983, abandoned.

[30] Foreign Application Priority Data

Apr. 1, 1983 [IT] Italy ............................... 20538 A/83

[51] Int. Cl.$^5$ ............................................ C07C 69/74
[52] U.S. Cl. .................................................... 560/118
[58] Field of Search ...................... 560/118; 260/501.1

[56] References Cited

U.S. PATENT DOCUMENTS 3,156,725  11/1964  Kaiser et al. ..................... 260/501.1
3,274,248   9/1966  Haranyi et al. .................. 260/501.1
3,700,675  10/1972  Turbanti ............................. 560/118

Primary Examiner—Michael L. Shippen
Attorney, Agent, or Firm—McAulay, Fisher, Nissen, Goldberg & Kiel

[57] ABSTRACT

For the preparation of derivatives of 2-diethylamino-1-methylethyl cis-1-hydroxy-(bicyclohexyl)-2-carboxylate, particularly the citrate, maleate, fumarate and pamoate, the oily base is initially converted to the phosphate, whereby solid products are obtained, both soluble and insoluble in water.

4 Claims, No Drawings

PROCESS FOR THE PREPARATION OF DERIVATIVE OF 2-DIETHYLAMINO-1-METHYLETHYL-1-HYDROXY-(BICYCLOHEXYL)-2-CARBOXYLATE

This application is a continuation of application Ser. No. 027,085, filed Mar. 16, 1987, which is a continuation of application Ser. No. 479,646 filed on Mar. 28, 1983, both now abandoned.

BACKGROUND OF THE INVENTION

The present invention relates to pharmaceutically acceptable salts of 2-diethylamino-1-methylethyl cis-1-hydroxy-(bicyclohexyl)-2-carboxylate and particularly to a process for their preparation.

2-diethylamino-1-methylethyl cis-1-hydroxy-(bicyclohexyl)-2-carboxylate, also known by the common international name of Rociverine or "Rociverinum", is in therapy as an antispasmodic drug (U.K. Patent No. 1.167.386).

It is prepared by reacting cis-1-hydroxy-(biciclohexyl)-2-carboxylic acid with 1-diethylamino-2-chloropropane in the presence of an acceptor of hydrogen chloride; by this reaction a mixture of position isomers is formed. It is then subjected to a thermal treatment which causes isomerization to take place. Thereafter, the product is purified by distillation (see Italian Patent Application No. 30163 A/78), the therapeutically active and desired isomer is obtained, having the formula:

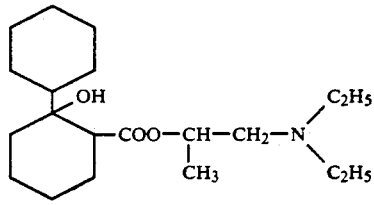

(I)

The thus obtained prrduct is in the form of a yellow oily liquid, not soluble in water, having a gaschromatographic purity of 98%, which is used as such in the pharmaceutical practice for the preparation of vials, tablets and suppositories. Of course, for pharmaceutical use, an oily substance is more difficult to handle, both in the preparation of the desired formulations, and as regards its storage, unless particular care is taken.

OBJECTS AND SUMMARY OF THE INVENTION

The main object of the present invention is to provide a process permitting the subject active principle to be obtained in form of a solid having a purity higher than 99%, with physical properties suitable for therapeutical use, namely either solubility in water for readily absorbable preparations or poor solubility for delayed release compositions.

Another object of the present invention is to provide a process permitting the preparation of a pharmaceutically acceptable solid salt, also starting from the reaction mixture resulting from preparation of active principle as previously mentioned, but after the thermal treatment, whereby the purification by distillation is no longer needed.

These and other objects are achieved by a process comprising reacting 2-diethylamino-1-methylethyl cis-1-hydroxy-(bicyclohexyl)-2-carboxylate with phosphoric acid in an organic solvent and at a low temperature, extracting with an organic solvent the base, i.e., the free rociverine from the alkali aqueous solution and salifying with pharmaceutically acceptable organic acids, in an organic solvent and at low temperature, or by treatment of the aqueous solution of the phosphate salt of rociverine with an aqueous solution of disodium pamoate.

Preferably, the reaction with phosphoric acid is carried out in acetone at a reaction temperature between 0° C. and −20° C. The salification with citric acid can be carried out at a temperature between 0° C. and +5° C.

The process is based on salification with phosphoric acid, dissolved in a suitable solvent, for instance acetone, of the rociverine base, either raw or distilled, the latter being also dissolved in a suitable solvent. Upon cooling a white crystalline solid is obtained, highly soluble in water, stable and not hygroscopic, having a melting point of 89°-92° C. and a gaschromatographic purity higher than 99%.

The pharmaceutically useful salts of rociverine, with a purity higher than 99%, are obtained by starting from rociverine phosphate, extracting with a suitable solvent, for instance, ethyl ether, the base after alkalizing the aqueous solution of the phosphate, salifying with the desired acid, such as citric, maleic or fumeric, in anhydrous form, dissolved in a suitable solvent, for instance, acetone, cooling. The salt with pamoic acid is obtained by mixing the aqueous solution of rociverine phosphate with an aqueous solution of disodium pamoate.

In the case of the rociverine citrate, a white powder, highly soluble in water and very slightly hygroscopic, is obtained, having a melting poing of 82°-84° C. and gaschromatographic purity higher than 99%.

In the case of rociverine maleate, there is obtained a white crystalline powder, highly soluble in water and very slightly hygroscopic, having melting point of 79°-81° C.

In the case of rociverine fumarate, there is obtained a white crystalline powder, soluble in water and non hygroscopic, having a melting point of 111°-113° C.

In the case of rociverine pamoate, there is obtained a white powder, not soluble in water, non hygroscopic and having a melting point of 103°-105° C.

The following examples, given by way of illustration only describe the process of the invention by reference to the citrate, it being understood that for the other pharmaceutically acceptable salts (apart from pamoate) the process is carried out likewise.

EXAMPLE 1

In a three-neck flask, having a stirrer and drop funnel, 339 g of 2-(diethylamino)-1-methylethyl cis-1-hydroxy-(bicyclohexyl)-2-carboxylate (rociverine) are dissolved in 250 mls of acetone and the flask is placed in a cooling bath at a temperature of between 0° C. and −20° C.

There are dropwise added under stirring over about 30 minutes 115 g of 85% phosphoric acid dissolved in 300 mls of acetone.

Upon completion of the addition, the mixture is stirred for 2 hours.

The precipitated product is filtered, washed with acetone and dried in an oven under vacuum. Rociverine phosphate is obtained as a microcrystalline solid having a melting point of 89°-92° C. with gaschromatographic titre of 99% and a yield of 93%.

EXAMPLE 2

432 g of rociverine phosphate are dissolved in 2 parts of water, and the mixture is made basic with an aqueous solution of sodium hydroxide and extracted with a suitable solvent, for instance ethyl ether; the ether is then dried over anhydrous sodium sulphate, cooled to 0° to 5° C., and added under stirring to 192 g of citric acid dissolved in the minimum amount of acetone.

The mixture is stirred for a minimum of 2 hours, so as to permit the salt to completely precipitate. The salt is filtered, washed with the same solvent and dried under vacuum.

There is thus obtained a yield of over 95% of rociverine citrate in the form of a white powder, very which is slightly hygroscopic, having a melting point of 82°–84° C. and a gaschromatographic purity higher than 99%.

EXAMPLE 3

Starting again with 432 g of rociverine phosphate the process of example 2 is repeated, by adding under stirring to the ethereal solution of the base, cooled at 0° C. to 5° C., 116 g of fumaric acid (or 116 g of maleic acid) dissolved in the minimum amount of acetone.

The isolation is then carried out as described in example 2, giving in this case a yield higher than 95% of rociverine fumarate as a white, non hygroscopic powder, having a melting point of 111°–113° C. and gaschromatographic purity higher than 99%; in the case of maleic acid, there is obtained a white crystalline powder, very little hygroscopic, having a melting point of 79° to 81° C.

EXAMPLE 4

A solution of 432 g of rociverine phosphate in 20 parts of water is slowly added with stirring to a solution obtained by dissolving 194,2 g of pamoic acid in 3 liters of water containing 40 g of NaOH. The thus formed precipitate is collected and washed by suspending it again in water.

The mixture is filtered to give a yield of 95% of a yellowish powder comprising a compound formed by two molecules of rociverine and one molecule of pamoic acid, with a melting point of 103°–105° C. It is important to point out that the rociverine phosphate has no substantial therapeutical properties, whereby the preparation thereof would not have had any therapeutical purpose. Likewise, was not obvious that by preparing the phosphate salt and then converting it into another pharmaceutically acceptable salt, as the citrate, the objects of the present invention would be achieved, since the direct preparation of rociverine citrate was giving a product having different properties and physical characteristics. Furthermore, in the process of the invention, namely, the step of conversion to the phosphate permits novel compounds to be prepared, which are therapeutically active namely, the fumarate, maleate and pamoate, which are not directly obtainable from the base, even if it is distilled.

I claim:

1. A process for the preparation of the citrate, maleate, or fumarate of 2-diethylamino-1-methylethyl cis-1-hydroxy-(bicyclohexyl)-2-carboxylate consisting essentially of the following steps:
   (a) reacting cis-1-hydroxyl-(bicyclohexyl)-2-carboxylic acid with 1-diethylamino-2-chloropropane in the presence of a hydrogen chloride acceptor; and then
   (b) subjecting the reaction product obtained from step (a) to a thermal treatment to cause isomerization; and then
   (c) reacting the material obtained from step (b) with phosphoric acid; and then
   (d) separating a solid crystalline product from the reaction mixture obtained from step (c);
   (e) treating the solid crystalline product obtained from step (d) with a base;
   (g) reacting the product from step (e) with an organic acid selected from the group consisting of citric acid, maleic acid and fumaric acid to form a crystalline precipitate of the corresponding salt.

2. A process according to claim 1, wherein said reaction with phosphoric acid is carried out in acetone and the reaction temperature is between 0° C. and −20° C.

3. A process according to claim 1, wherein said treating with base is carried out with an alkali hydroxide and said extraction is carried out with ethyl ether.

4. A process according to claim 1, wherein said treating with acid is carried out with citric acid in acetone and at a temperature between 0° C. and 5° C.

* * * * *